(12) United States Patent
Mower

(10) Patent No.: US 7,776,365 B2
(45) Date of Patent: *Aug. 17, 2010

(54) ARTICLE WITH SKIN PROTECTING AND MOISTURIZING COMPOUND

(75) Inventor: Thomas E. Mower, Payson, UT (US)

(73) Assignee: Sakura Properties, LLC, Salem, UT (US)

( * ) Notice: Subject to any disclaimer, the term of this patent is extended or adjusted under 35 U.S.C. 154(b) by 1057 days.

This patent is subject to a terminal disclaimer.

(21) Appl. No.: 11/307,032

(22) Filed: Jan. 19, 2006

(65) Prior Publication Data

US 2006/0210516 A1 Sep. 21, 2006

Related U.S. Application Data

(63) Continuation-in-part of application No. 11/083,826, filed on Mar. 18, 2005.

(51) Int. Cl.
A01N 65/00 (2009.01)
(52) U.S. Cl. .................................................. 424/725
(58) Field of Classification Search ........................ None
See application file for complete search history.

(56) References Cited

U.S. PATENT DOCUMENTS

| | | | |
|---|---|---|---|
| 1,607,844 A | 11/1926 | Neilsen | |
| 1,687,625 A | 10/1928 | Mackenzie | |
| 2,933,431 A | 4/1960 | Sperouleas | |
| 3,240,775 A | 3/1966 | Schweiger | |
| 3,264,188 A | 8/1966 | Gresham | |
| 3,301,746 A | 1/1967 | Sanford | |
| 3,697,287 A | 10/1972 | Wintz | |
| 3,700,623 A | 10/1972 | Keim | |
| 3,741,273 A | 6/1973 | Meade | |
| 3,772,076 A | 11/1973 | Keim | |
| 3,911,105 A | 10/1975 | Papantoniou et al. | |
| 4,009,313 A | 2/1977 | Crawford | |
| 4,112,167 A | 9/1978 | Dake | |
| 4,139,619 A | 2/1979 | Chidsey | |
| 4,481,243 A | 11/1984 | Allen | |
| 4,556,560 A | 12/1985 | Buckingham | |
| 4,596,812 A | 6/1986 | Chidsey | |
| 4,670,285 A | 6/1987 | Clandinin | |
| 4,698,360 A | 10/1987 | Masquelier | |
| 4,871,550 A | 10/1989 | Millman | |
| 4,996,044 A | 2/1991 | Mercado | |
| 4,996,238 A | 2/1991 | Matravers | |
| 5,021,245 A | 6/1991 | Borschel | |
| 5,059,686 A | 10/1991 | Sau | |
| 5,152,983 A | 10/1992 | Nambudiry | |
| 5,165,933 A | 11/1992 | Oishi | |
| 5,292,538 A | 3/1994 | Paul | |
| 5,362,488 A | 11/1994 | Sibley | |
| 5,397,786 A | 3/1995 | Simone | |
| 5,409,703 A | 4/1995 | McAnalley | |
| 5,415,879 A | 5/1995 | Oh | |
| 5,541,166 A | 7/1996 | Parish et al. | |
| 5,631,032 A | 5/1997 | Gil | |
| 5,672,339 A | 9/1997 | Soyama et al. | |
| 5,700,590 A | 12/1997 | Masor | |
| 5,720,966 A | 2/1998 | Ostendorf | |
| 5,733,572 A | 3/1998 | Unger | |
| 5,762,945 A | 6/1998 | Ashley | |
| 5,776,494 A | 7/1998 | Guskey | |
| 5,814,188 A | 9/1998 | Vinson | |
| 5,834,044 A | 11/1998 | Schmitz | |
| 5,861,048 A | 1/1999 | Kamasaka | |
| 5,891,888 A | 4/1999 | Strahl | |
| 5,980,922 A | 11/1999 | Mackey | |
| 6,033,887 A | 3/2000 | Champagne | |
| 6,051,235 A | 4/2000 | Theuer | |
| 6,051,236 A | 4/2000 | Portman | |
| 6,077,557 A | 6/2000 | Gordon et al. | |
| 6,190,724 B1 | 2/2001 | Sawatzki et al. | |
| 6,268,182 B1 | 7/2001 | Kamasaka | |
| 6,346,237 B2 | 2/2002 | Lemann | |
| 6,447,817 B1 | 9/2002 | Niyiro | |
| 6,517,849 B1 * | 2/2003 | Seger et al. ................. | 424/402 |
| 6,521,240 B1 | 2/2003 | Minerath | |
| 6,573,250 B2 | 6/2003 | Umeda | |
| 6,589,537 B2 | 7/2003 | Harbeck | |
| 6,602,869 B1 | 8/2003 | Galey | |

(Continued)

FOREIGN PATENT DOCUMENTS

EP 1199942 5/2002

(Continued)

OTHER PUBLICATIONS

Bank, Ginny and Schauss, Alex, Antoxidant Testing; an ORAC Update. www.nutraceuticalsworld.com, Mar. 2004.

(Continued)

Primary Examiner—Michael V Meller
(74) Attorney, Agent, or Firm—Clayton, Howarth & Cannon, P.C.

(57) ABSTRACT

An article with skin-protecting and moisturizing compound, comprising a tissue substrate, a base and partially hydrolyzed fucoidan. The partially hydrolyzed fucoidan may be sulfonated. The partially hydrolyzed fucoidan may be derived from Tongan limu moui seaweed, Japanese wakame seaweed, Japanese mozuku seaweed, or combinations thereof.

4 Claims, No Drawings

U.S. PATENT DOCUMENTS

| | | | |
|---|---|---|---|
| 6,616,950 | B2 | 9/2003 | Pushpangadan |
| 6,641,848 | B1 | 11/2003 | Bonte |
| 6,656,903 | B1 | 12/2003 | Sawatzki |
| 6,673,755 | B2 | 1/2004 | Wei |
| 6,693,209 | B2 | 2/2004 | Van Es et al. |
| 6,703,027 | B2 | 3/2004 | Kurosawa |
| 6,730,333 | B1 | 5/2004 | Garrity |
| 6,812,220 | B2 | 11/2004 | Jackson et al. |
| 6,863,918 | B2 | 3/2005 | Bindels |
| 6,890,543 | B2 | 5/2005 | Minami |
| 6,896,766 | B2 | 5/2005 | Sarbo |
| 2002/0028230 | A1* | 3/2002 | Eichhorn et al. ............ 424/443 |
| 2002/0076431 | A1 | 6/2002 | Umeda |
| 2002/0197352 | A1 | 12/2002 | Portman |
| 2003/0039670 | A1* | 2/2003 | Mizutani et al. ............ 424/401 |
| 2003/0045572 | A1 | 3/2003 | Niyiro |
| 2003/0064958 | A1 | 4/2003 | Jackson et al. |
| 2003/0083209 | A1 | 5/2003 | Moodycliffe |
| 2003/0207004 | A1 | 11/2003 | Theuer |
| 2004/0043961 | A1 | 3/2004 | Wu |
| 2004/0077523 | A1 | 4/2004 | Ochiai et al. |
| 2004/0180850 | A1 | 9/2004 | Natunen |
| 2004/0242665 | A1 | 12/2004 | Boulle |
| 2005/0013871 | A1 | 1/2005 | Niazi |
| 2005/0015854 | A1 | 1/2005 | Eisenberg |
| 2005/0019356 | A1 | 1/2005 | Bissett |
| 2005/0053713 | A1 | 3/2005 | Birch |
| 2005/0058672 | A1 | 3/2005 | Gupta |
| 2005/0058674 | A1 | 3/2005 | Joseph |
| 2005/0058833 | A1 | 3/2005 | Krzysik |
| 2005/0064070 | A1 | 3/2005 | Liebrecht |
| 2005/0095260 | A1 | 5/2005 | Pardoe |
| 2005/0095320 | A1 | 5/2005 | Botteri |
| 2005/0096295 | A1 | 5/2005 | McMahon |
| 2005/0100636 | A1 | 5/2005 | Botteri |
| 2005/0129708 | A1 | 6/2005 | Fujii et al. |
| 2005/0137175 | A1 | 6/2005 | Bernard |
| 2005/0147732 | A1 | 7/2005 | Schwach-Abdellaoui |
| 2005/0191405 | A1 | 9/2005 | Okos |
| 2005/0192218 | A1 | 9/2005 | Ellis et al. |
| 2005/0214332 | A1 | 9/2005 | Osborne et al. |
| 2005/0214383 | A1 | 9/2005 | Bubnis et al. |
| 2005/0220828 | A1 | 10/2005 | Ullom |
| 2005/0230069 | A1 | 10/2005 | Hilbig |
| 2005/0232876 | A1 | 10/2005 | Minga |
| 2005/0239749 | A1 | 10/2005 | Kambayashi |
| 2005/0244369 | A1 | 11/2005 | Georgiades |
| 2006/0292255 | A1* | 12/2006 | Moffett et al. ............ 424/769 |

FOREIGN PATENT DOCUMENTS

| | | |
|---|---|---|
| EP | 0846422 | 5/2003 |
| JP | 3225923 | 8/2001 |

OTHER PUBLICATIONS

Oliver Starr, Tumeric Phytonutrient Protection for a Variety of Physiological Stresses, VRPs Nutritional News, May/Jun. 1996.

Marilyn Sterling, Proanthocyanidin Power, Nutrition Science News, Jun. 2000.

High-ORAC Foods May SLow Aging, Agricultural Research, Feb. 2005.

Substituting Isosorbides for Phthalates, yet2.com, Dec. 2004.

Novel Plasticizers to Replace Phthalates in PVC or Other Plastics, yet2.com. http://www.yet2.com/app/list/techpak?id=33822&sid=20&abc=0, Mar. 2005.

Hwan Su Yoon, Ju Yeo Lee, Sung Min Boo, Debashish Bhattacharya, Phylogny of Alariaceae, Laminariaceae, and Lesoniaceae (RuBisCo Spacer and Nuclear-Encoded ITS Sequence Comparisons, Molecular Phylogenitics and Evolution, Nov. 2001, vol. 21, No. 2, pp. 231-243.

Sakait, Ishizukak., Kato, I, Isolation and Characterization of a Fucoidan-Degrading Marine Bacterium, Mar Biotechnical, Sep.-Oct. 2003.

Rita Elkins, Prize Sea Plant of Tonga and the South Pacific—Limu Moui, 2001.

Berteua, Oliver and Mulloy, Barbara, Sulfonated fucans, fresh perspectives; structures, funtions, and biological properties of sulfated fucans and an overview of enzymes active toward this class of polysaccharide, Glycobiology, vol. 13, No. 6, Mar. 2003.

Del Bigio, Mr. Yan HJ, Campbell, TM, Peeling, J., Effect of Fucoian Treatment on Collagenase-induced Intracerebral Hemorrhage in rats, Annual Mtg. and Food Expo., Anaheim, CA, Jun. 1999.

Shibata, H., Imuro, M., Uhiya N., Kawamori, T., Nagaoka, M., Yeyama S., Hashimoto S., Yokokura T., Sugimura T., Wakabi Ashi K., Preventive Effects of Cladosiphon Fucoidan Against *Helicobacter pylori* Infection in Mongolian Gerbils, PubMed, Feb. 2003.

A.I., Usov, G.P. Smrinova, N. G. Klochkova, Polysaccharides of Algae: Polysaccharide Composition of Several Brown Algae From Kamchatka, 27 Russian Journal of Bioorganic Chemistry, vol. 27, No. 6, pp. 395-399, Jun. 2001.

Berangere, Tissot, Regis, Daniel, Biological Properties of Sulfated Fucans; the Potent Inhibiting Activity of Algal Fucoidan Against the Human Complement System, Glycobiology, vol. 13, No. 12, Dec. 2003.

Matou S., Helley D., Chabut D, Bros A Fischer AM, Effect of Fucoidan on Fibroblast Growth Factor-2 induced Angiogenesis in Vitro Elsevier Science, May 15, 2002.

Takara-Takara Kombu Fucoidan (Functional Seaweed Dietary Fiber), Jan. 2006.

Soeda S, Kozako T. Iwata K., Himeno H., Oversulfated Fucoidan Inhibits the Basic Fibroblast Growth Factor-induced Tube Formation by Human Umbilical Vein Endothelial Cells; Its Possible Mechanism of Action, Department of Biochemistry, Faculty of Pharmaeutical Sciences, Fukuoka University, Jun. 2, 2002.

A Guide to the Seaweed Industry, FAO Fisheries Technical Paper 441, Jun. 2003.

Herworld—Back to Basics—http://www.herworld.com/Beauty_report.html, Oct. 2005.

Desitin—http://www.desitin.com/en/?dsp=21&psp=20, Nov. 2005.

Desitin Creamy—http://www.desitin.com/en/?dsp=22&psp=20, Nov. 2005.

Boudreauxs Butt Paste—http://www.skinstore.com/store/product.asp?catID=422&prodID=514, Nov. 2005.

Johnson's Baby Oil—http://www.johnsonsbaby.com/products/oil/baby-oil, Nov. 2005.

Johnson's Creamy Baby Oil—http://www.johnsonsbaby.com/products/oil/creamy-baby-oil, Nov. 2005.

Johnson' Baby Oil Gel with Aloe Vera and Vitamin E—http://www.johnsonsbaby.com/products/oil/baby-oil-with-aloe, Nov. 2005.

Pediatric Products Similac Advance—http://rpdcon40.ross.com/pn/PediatricProducts.NSF/0/706d4b6080c6E7C085256BA30052E1D1?OpenDocument, Nov. 2005.

Marquardt, Thorsten; Luhn, Kerstin; Srikrishna, Geetha; Freeze, Hudson H; Harms, Erik; Vestweber, Dietmar, Correction of Lukocyte Adhesion Deficiency Type II With Oral Fucose—Blood vol. 94, No. 12, (Dec. 15) 1999 pp. 3976-3985.

Russian Adaptogens: Health Secrets Revealed—http://members.tripod.com/macyuen-ivil/id13.html (Dec. 2004).

Polysaccharide Found in the Seaweed Kombu, U-Foucoidan, Discovered to Cause Cancer Cells to self Destruct (Jun. 17, 1996).

* cited by examiner

ARTICLE WITH SKIN PROTECTING AND MOISTURIZING COMPOUND

This application is a Continuation-in-Part of, and claims the benefit of application Ser. No. 11/083,826, filed on 18 Mar. 2005, by Thomas E. Mower, entitled Fucoidan Compositions and Methods for Dietary and Nutritional Supplements, the entirety of which is herein incorporated by reference.

BACKGROUND OF THE INVENTION

1. Field of the invention

The present invention relates to articles with skin-protecting and moisturizing compound, specifically wherein the compound includes partially hydrolyzed fucoidan.

2. Description of the Related Art

The skin is made up of two major layers. The epidermis is the top layer and forms a protective covering for skin and controls the flow of water and substances in and out of the skin. To stay healthy, the skin has to cope with changing environmental conditions and repair damage at the same time. The skin is in a constant state of repair as it sheds the dead cells on the surface and replenishes the lower layers. The dermis is the lower level of the skin and is the layer that provides the strength, elasticity, and thickness to the skin. Cells in the dermis are responsible for synthesis and secretion of all the dermal matrix components, such as collagen, elastin, and glycosaminoglycans. Collagen provides the strength, elastin the elasticity, and glycosaminoglycans the moistness and plumpness of the skin.

The stratum corneum is the outer-most layer of the skin and is responsible for regulating skin water levels and functioning as a barrier against chemicals and other stressors found in the environment. The complex arrangement of lipids in the intercellular space of the stratum corneum is responsible for the establishment of normal barrier function. Multi-layered structures of cholesterol, ceramides, and fatty acids, as well as some other minor lipids, provide the major barrier to the transport of hydrophilic substances into or through the skin. The link between the barrier function and skin health is apparent from the skin inflammation caused by lipid extraction from the skin.

Skin barrier can be damaged due to a number of mechanisms. One mechanism for damage is physical abrasion, which may be caused by repeated rubbing of tissue products, such as facial or bath tissue, on the skin. With physical abrasion, layers of the skin are stripped away causing damage to the stratum corneum. Also, biological fluids, such as urine, feces, nasal and vaginal secretions, may contain a variety of components that can damage the stratum corneum. Some specific examples include proteases, lipases, bile acids, and fatty acids. Once the stratum corneum barrier is compromised, skin inflammation can occur.

The skin may be abused by soaps, emulsifier-based cosmetics, hot water, or organic solvents, for example. These each contribute to rob the skin of essential moisture, and to create a stressed barrier that does not function properly. Moisture loss and irritation increases, leaving the skin sensitive, scaly, and dry. Free-radical activity multiplies, causing more wrinkles and premature aging.

Furthermore, the skin is subject to deterioration through dermatological disorders, environmental abuse, such as from wind, air conditioning, and central heating, or through the normal aging process, which may be accelerated by exposure of skin to sun. The thickness of the dermal layer is reduced due to aging, thus causing the skin to slacken. This is believed to be partially responsible for the formation of wrinkles. In recent years, the demand for cosmetic compositions and cosmetic methods for improving the appearance and condition of skin has grown enormously.

Excessive hydration of the skin can also have a negative impact on skin barrier. The hydration level of diapered skin, for example, may reach between five and ten times that of undiapered skin. Frequent contact of diapered skin with fluids such as urine and feces may also contribute to increased hydration. Increased skin hydration disrupts skin lipid organization in the stratum corneum, and may increase the skin permeability of irritants, thus increasing the risk of skin inflammation.

Tissue products, such as bath and facial tissue, are commonly used to absorb body fluids and leave the skin dry. These products, in addition to absorbing and wiping fluids, however, also abrade the skin during use and frequently do not leave the skin completely dry and free of the body fluid after use. During frequent use of these products, the skin can become so dry and/or abraded as to appear red and be sore to the touch. To reduce this problem, additive formulations have been applied to tissue products to provide lubricity and moisture. Once deposited on the skin, these products may provide a skin benefit by occluding the skin and protecting the stratum corneum until the damage is repaired.

To date, the moisturizing and/or lubricating formulations applied to tissue products have not been completely satisfactory. Many formulations to date have proven to be unstable, even at slightly elevated temperatures and have tended to migrate into the product matrix prior to use where the formulation is only of minimal, if any benefit. Additionally, many formulations used to date have had very poor transfer rates from the product to the skin where it can be of use. As such, it is apparent that there is a commercial need for hydrophilic lubricating formulations suitable for use in combination with tissue products, such as facial tissue and bath tissue. It would be advantageous if the lubricating formulation could provide a moisturization benefit to alleviate skin dryness, as well as present a soft, aesthetically pleasing feel to reduce friction between the product and skin. Also, it would be advantageous if the lubricating formulations were formulated to be fluid during processing and rapidly solidify after application to the products.

Several U.S. Patents and Patent Application Publications have disclosed the addition of a lotion or moisturizing agent to a tissue. For example, Joseph, in U.S. Patent Application Publication No. 2005/0058693 discloses tissue products comprising a moisturizing and lubricating composition. The moisturizing and lubricating composition comprises an emollient, a humectant, and immobilizing agent and a compatibilizing agent. Optionally, the moisturizing and lubricating compositions can comprise a dispersing agent, or other components.

In another example, U.S. Patent Application Publication No. 2005/0230069, Hilbig discloses a paper tissue such as a facial tissue or a disposable handkerchief and a method for making a tissue paper product from a tissue paper web. The method comprises the steps of passing the tissue paper web through an embossing nip formed between a first and a second embossing roll, wherein at least one of the embossing rolls comprises at least 30 embossing elements per square centimeter; and passing the tissue paper web through a calendering nip formed between a first and a second calendering roll, wherein the first and the second calendering roll are in contact with the tissue paper web over a contact length measured parallel to the direction of the axis of the first calendering roll exert a pressure onto the paper web of at least 50 N per centimeter of the contact length.

In yet another example, U.S. Pat. No. 2,933,431, Sperouleas discloses medicated tissue. The tissues are to be applied to the nose and produce medicinal vapors for the alleviation of distress occasioned by nasal, throat, or bronchial ailments.

Consumers are increasingly seeking anti-aging cosmetic products that treat or delay the visible signs of actual aging and weathered skin, such as wrinkles, lines, sagging, hyperpigmentation, and age spots. Consumers also frequently seek other benefits from cosmetic products in addition to anti-aging. The concept of sensitive skin has raised the demand for cosmetic products that improve the appearance and condition of sensitive, dry, and flaky skin and soothe red or irritated skin. Consumers also desire cosmetic products that treat spots, pimples, blemishes, and so forth.

Research shows that using a skin care product that includes the skin's natural building blocks speeds the skin's ability to repair itself and keeps the barrier function of skin at optimal levels. This approach treats the problem, not merely the symptom. Irritation stops before it may start, so recurring problems are avoided, thus bringing the skin back to ideal conditions.

Consumer demand for natural-based products has been growing in recent years. Chemical synthesis is perceived as environmentally unsafe. A chemically synthesized ingredient may contain harsh chemicals. Natural products are perceived as more pure and mild, and thus superior to chemically synthesized products. Delivering a cosmetic benefit from plant sources, however, is not trivial. To derive a real benefit from a natural source, not only does a plant or a part of the plant containing a specific active ingredient have to be identified, but a minimum concentration and/or a specific extract of that plant has to be identified that truly delivers a cosmetic benefit.

Accordingly, consumers demand an effective treatment for the skin and wrinkles that moisturizes, heals, and soothes the vulnerable and delicate surface of the skin. Further, consumers demand that treatment for the skin be based on natural products to promote healing and preserve youthful appearance.

Fucoidan is a sulfated polysaccharide found in many sea plants and animals, and is particularly concentrated in the cell walls of brown algae (*Phaeophyceae*). Fucoidan is a complex carbohydrate polymer composed mostly of sulfated L-fucose residues. These polysaccharides are easily extracted from the cell wall of brown algae with hot water or dilute acid and may account for more than 40% of the dry weight of isolated cell walls. O. Berteau & B. Mulloy, *Sulfated Fucans, Fresh Perspectives: Structures, Functions, and Biological Properties of Sulfated Fucans and an Overview of Enzymes Active Toward this Class of Polysaccharide*, 13 *Glycobiology* 29R-40R (2003). Fucoidan structure appears to be linked to algal species, but there is insufficient evidence to establish any systematic correspondence between structure and algal order. High amounts of α (1-3) and α (1-4) glycosidic bonds occur in fucoidans from *Ascophyllum nodosum*. A disaccharide repeating unit of alternating α (1-3) and α (1-4) bonds represents the most abundant structural feature of fucoidans from both *A. nodosum* and *Fucus vesiculosus* which are species of seaweed. Sulfate residues are found mainly in position 4. Further heterogeneity is added by the presence of acetyl groups coupled to oxygen atoms and branches, which are present in all the plant fucoidans. Following is a representation of *A. nodosum* fucoidan:

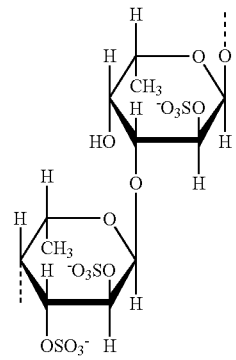

Fucoidan-containing seaweeds have been eaten and used medicinally for at least 3000 years in Tonga and at least 2000 years in China. An enormous amount of research has been reported in the modern scientific literature, where more than 500 studies are referenced in a PubMed search for fucoidan.

The physiological properties of fucoidans in the algae appear to be a role in cell wall organization and possibly in cross-linking of alginate and cellulose and morphogenesis of algal embryos. Fucoidans also have a wide spectrum of activity in biological systems. They have anticoagulant and antithrombotic activity, act on the inflammation and immune systems, have antiproliferative and antiadhesive effects on cells, and have been found to protect cells from viral infection.

Further, fucoidan has numerous beneficial functions that heal and strengthen different systems of the body, including anti-viral, anti-inflammatory, anti-coagulant, and anti-tumor properties. A. I. Usov et al., *Polysaccharides of Algae: Polysaccharide Composition of Several Brown Algae from Kamchatka*, 27 *Russian J. Bio. Chem.* 395-399 (2001). Fucoidan has been found to build and stimulate the immune system. Research has also indicated that fucoidan reduces allergies, inhibits blood clotting, fights diabetes by controlling blood sugar, prevents ulcers, relieves stomach disorders, reduces inflammation, protects the kidneys by increasing renal blood flow, and detoxifies the body. Fucoidan also helps to reduce and prevent cardiovascular disease by lowering high cholesterol levels and activating enzymes involved in the beta-oxidation of fatty acids.

A Japanese study found that fucoidans enhanced phagocytosis, the process in which white blood cells engulf, kill, digest, and eliminate debris, viruses, and bacteria. An American study reported that fucoidans increased the number of circulating mature white blood cells. An Argentine study and a Japanese study found that fucoidans inhibited viruses, such as herpes simplex type 1, from attaching to, penetrating, and replicating in host cells. A Swedish study is among the many that showed fucoidans inhibit inflammation cascades and tissue damage that may lead to allergies. Other studies, such as one in Canada, found that fucoidans block the complement activation process that is believed to play an adverse role in chronic degenerative diseases, such as atherosclerosis, heart attack, and Alzheimer's disease. Two American studies found that fucoidans increase and mobilize stem cells.

Researchers have also determined that fucoidan tends to combat cancer by reducing angiogenesis (blood vessel growth), inhibiting metastasis (spreading of cancer cells to other parts of the body), and promoting death of cancer cells. Certain societies that make brown seaweed part of their diet appear to have remarkably low instances of cancer. For example, the prefecture of Okinawa, where the inhabitants enjoy some of the highest life expectancies in Japan, also happens to have one of the highest per capita consumption rates of fucoidans. It is noteworthy that the cancer death rate in Okinawa is the lowest of all the prefectures in Japan.

Brown seaweed, a ready source of fucoidan, is found in abundance in various ocean areas of the world. One of the purest locations that provides some of the highest yields of fucoidan is in the clear waters surrounding the Tongan islands, where the seaweed is called limu moui. In Japan, hoku kombu (Laminaria japonica), is said to be particularly rich in fucoidans and is similar to limu moui. The Japanese also consume at least two other types of brown seaweed-wakame and mozuku (Cladosiphon and Nemacystus).

Typically, about four percent by weight of Tongan limu moui is fucoidan. There are at least three types of fucoidan polymer molecules found in brown seaweed. U-fucoidan, having about 20 percent glucuronic acid, is particularly active in carrying out cancer cell destruction. F-fucoidan, a polymer of mostly sulfated fucose, and G-fucoidan both tend to induce the production of HGF cells that assist in restoring and repairing damaged cells. All three types of fucoidan also tend to induce the production of agents that strengthen the immune system.

What is needed is an article with a skin-protecting and moisturizing compound that solves one or more of the problems described herein and/or one or more problems that may come to the attention of one skilled in the art upon becoming familiar with this specification. One such problem that is not solved by the cited prior art is the use of a natural component in an article to assist in regeneration, healing, and/or reverses skin damage. Another such problem includes providing an article that assists in anti-aging, regeneration of cells, promoting youthfulness, reducing inflammation, minimizing visible signs of biological and/or environmental aging, and/or fighting free radicals using anti-oxidants.

SUMMARY OF THE INVENTION

The present invention has been developed in response to the present state of the art, and in particular, in response to the problems and needs in the art that have not yet been fully solved by currently available articles with skin-protecting and moisturizing compounds. According to one embodiment of the present invention is an article with skin-protecting and moisturizing compound, which includes an article substrate, a base and partially hydrolyzed fucoidan.

The partially hydrolyzed fucoidan may be a derivative of one of the group consisting of: Tongan limu moui seaweed, Japanese wakame seaweed, Japanese mozuku seaweed, and combinations thereof. The fucoidan may be sulfonated. The partially hydrolyzed fucoidan may be from about 0.05 weight percent to about 50 weight percent of the article. The article may further include an anti-viral agent. The anti-viral agent may be pyrrolidone carboxylic acid. The anti-viral agent may be a metal salt. The article may further include one of the additives selected from the group consisting of: honey, mangosteen, witch hazel, sage, piper, clove, ginger, red pepper, willow, rhubarb, sesame, chamomile, propolis, thyme, lavender, cinnamon oil, flower or blossom oils, olive oil, palm oil, coconut oil, beeswax, and combinations thereof.

According to another embodiment of the present invention is a method of making an article with skin-protecting and moisturizing compound, which method includes providing a first tissue paper web, applying a base to the first tissue paper web, and applying partially hydrolyzed fucoidan to the first tissue paper web. The method may further include the step of applying a second tissue paper web to the first tissue paper web. The method may further include applying an anti-viral agent to the first tissue paper web. The method may further include applying an anti-viral agent to the second tissue paper web. The base and the partially hydrolyzed fucoidan may be combined before application to the tissue paper web. The partially hydrolyzed fucoidan may be sulfonated. The partially hydrolyzed fucoidan may be a derivative of one of the group consisting of: Tongan limu moui seaweed, Japanese wakame seaweed, Japanese mozuku seaweed, and combinations thereof.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

DETAILED DESCRIPTION OF THE INVENTION

For the purposes of promoting an understanding of the principles of the invention, reference will now be made to the exemplary embodiments, and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to "one embodiment," "an embodiment," or similar language means that a particular feature, structure, or characteristic described in connection with the embodiment is included in at least one embodiment of the present invention. Thus, appearances of the phrases "one embodiment," "an embodiment," and similar language throughout this specification may, but do not necessarily, all refer to the same embodiment, different embodiments, or component parts of the same or different illustrated invention. Additionally, reference to the wording "an embodiment," or the like, for two or more features, elements, etc. does not mean that the features are related, dissimilar, the same, etc. The use of the term "an embodiment," or similar wording, is merely a convenient phrase to indicate optional features, which may or may not be part of the invention as claimed.

As used herein, "comprising," "including," "containing," "is," "are," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

Each statement of an embodiment is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The independent embodiments are considered to be able to be combined in whole or in part one with another as the claims and/or art may direct, either directly or indirectly, implicitly or explicitly.

Finally, the fact that the wording "an embodiment," or the like, does not appear at the beginning of every sentence in the specification, such as is the practice of some practitioners, is merely a convenience for the reader's clarity. However, it is the intention of this application to incorporate by reference the phrasing "an embodiment," and the like, at the beginning of every sentence herein where logically possible and appropriate.

As used herein, "partially hydrolyzed fucoidan" means fucoidan that has been hydrolyzed into smaller polymers and oligomers, but not so thoroughly hydrolyzed as to result in complete hydrolysis to substantially primarily monosaccharides.

As used herein, "lotions" are liquid cosmetics, often suspensions or dispersions, intended for external application to the body.

As used herein, "creams" are soft cosmetic-type preparations. Creams of the oil-in-water (O/W) type include preparations such as foundation creams, hand creams, shaving creams, and the like. Creams of the water-in-oil (W/O) type include cold creams, emollient creams, and the like. Pharmaceutically, creams are solid emulsions containing suspensions or solutions of active ingredients for external application. Generally, preparations of this type are classified as ointments. Specifically, they belong to the emulsion-type bases.

As used herein, "ointments" are semisolid preparations for external application of such consistency that may be readily applied to the skin. They should be of such composition that they soften, but not necessarily melt, when applied to the body. They serve as vehicles for the topical application of active ingredients and also function as protectives and emollients for the skin. For many years ointments were limited by definition and use to mixtures of fatty substances. Today, in addition to such oleaginous mixtures, there are ointment preparations possessing the same general consistency but entirely free of oleaginous substances. In many instances, they are emulsions of fatty or wax-like materials with comparatively high proportions of water. These emulsions may be either water-in-oil (W/O) or oil-in-water (O/W) emulsions, depending primarily on the selection of the emulsifying agent. Such semisolid emulsions are also referred to as creams. Creams and ointments containing large amounts of insoluble powders are referred to as pastes. Pastes are usually stiffer and more absorptive than creams and ointments.

The present invention advances prior art articles by providing an article with a skin-protecting and moisturizing compound formulated with fucoidan from seaweed, such as limu moui, kombu, or mozuku. The addition of fucoidan to the article of the present invention serves to provide significant advantages not found in prior art skin protection compositions. The fucoidan-enhanced articles of the present invention provides many beneficial functions, including providing for anti-aging, and regeneration of cells and tissues; promoting youthfulness; reducing inflammation and the like. In addition, the fucoidan-enhanced skin protection compositions of the present invention minimize the visible signs of both biological and environmental aging. That is, the present compositions may slow the aging process, assist in regenerating damaged cells and tissues, and promote growth factors in the body. Fucoidan is high in antioxidants that help to fight free radical damage to the body that may lead to cancer. These antioxidants help to fight free radical damage caused by the sun and other changing environmental conditions and elements.

The article with skin-protecting and moisturizing compound of the present invention includes an article, a base and partially hydrolyzed fucoidan.

The Article

The present invention is useful with tissue paper in general, including but not limited to conventionally felt-pressed tissue paper; high bulk pattern densified tissue paper; and high bulk, uncompacted tissue paper. It can be of a homogenous or multi-layered construction; and tissue paper products made therefrom can be of a single-ply or multi-ply construction. The tissue paper can have a basis weight of between about 10 $g/m^2$ and 130 $g/m^2$, or between about 20 $g/m^2$ and 80 $g/m^2$, or between about 25 $g/m^2$ and 60 $g/m^2$. Unless otherwise specified, all amounts and weights relative to the paper are on a dry basis.

The tissue of the present invention comprises at least one fibrous ply and may include two or more fibrous plies. The fibrous ply may be noncellulosic, or cellulosic, or a combination thereof. The fibrous ply may be layered. Each fibrous ply has two sides. Side one of the fibrous ply is generally oriented toward the user while side two of the fibrous ply is generally oriented away from the user. A base and partially hydrolyzed fucoidan according to the present invention can be applied to one or more of the fibrous plies. The base and partially hydrolyzed fucoidan may be applied to side one of the fibrous ply, side two of the fibrous ply, or both sides.

Conventionally pressed tissue paper and methods for making such paper are well known in the art. Such paper is typically made by depositing a papermaking furnish on a foraminous forming wire, often referred to in the art as a fourdrinier wire. Once the furnish is deposited on the forming wire, it is referred to as a web. The web is dewatered by pressing the web and drying at elevated temperature. The particular techniques and typical equipment for making webs according to the process just described are well known to those skilled in the art.

The Base

The hydrogen ion concentration is typically adjusted by adding an acid, according to methods well known in the art. An illustrative acid comprises sulfuric acid, and when sulfuric acid is used, the conditions can be selected such that available reactive groups created by partial hydrolysis of the fucoidan are sulfonated, resulting in a partially hydrolyzed, sulfonated fucoidan composition.

Ideally, an ointment base should be nonirritating, nondehydrating, nongreasy, compatible with active ingredients, stable, easily removable with water, absorptive (able to absorb water and/or other liquids), and able to efficiently release the incorporated active ingredients. Ointments may be classified according to type, based on composition. Such ointment classes include oleaginous bases, absorption bases, emulsion bases, and water-soluble bases.

Oleaginous bases are generally anhydrous, hydrophobic, insoluble in water, and are not water-removable. Oleaginous bases includes the early ointments, which consisted almost entirely of vegetable and animal fats, as well as petroleum hydrocarbons. Fixed oils of vegetable origin include olive, cottonseed, sesame, persic, and other oils. Hydrocarbon bases include ointments prepared from petrolatum or liquid petrolatum with wax or other stiffening agents. Hydrocarbon bases do not become rancid, which is an advantage compared to animal fats and vegetable oils. Another oleaginous base includes silicones, which are synthetic polymers in which the basic structure is an alternating chain of silicon and oxygen atoms (e.g., —O—Si—O—Si—O—Si—). Silicones used in the pharmaceutical and cosmetic industries include dimethylpolysiloxane, methylphenylpolysiloxane, and a stearyl ester of dimethylpolysiloxane, all of which are insoluble in water and are water repellant. Illustrative oleaginous bases are well known in the art, such as Silicone Gibson Base and Vanisil Silicone Ointmente.

Absorption bases are generally anhydrous, hydrophilic, insoluble in water, and most are not water-removable. These bases have the property of absorbing several times their weight of water and forming emulsions while retaining their ointment-like consistency. Absorption bases vary in their composition, but for the greater part, they are mixtures of animal sterols with petrolatum. Combinations of cholesterol and/or other lanolin fractions with white petrolatum are such absorption bases, and Eucerin® and Aquaphor® (available from Beirsdorf Aktiengesellschaft Corporation, Germany) were among the earliest commercial bases of this type. Zopf Emollient Cream, Hoch Formula, Hydrophilic Petrolatum Base, Wool Alcohols Base, and Aquabase Ointment are absorption bases described herein. Some commercially available absorption bases include Aquaphor® (Made by Duke Laboratories, South Norwalk, Conn.), Polysorb® (Made by Fougera, a division of Altana Inc, Melville, N.Y.), and Nivea® Cream (Made by Duke Laboratories, South Norwalk, Conn.).

Emulsion bases may be either W/O bases, which are hydrous, insoluble in water, and not removable with water and will absorb water, or O/W bases, which are hydrous, insoluble in water, and water-removable and will absorb water. These preparations are solid emulsions, and similar products have long been used as cosmetic creams. The availability of numerous compounds for use as wetting agents, dispersing agents, emulsifiers, penetrants, emollients, detergents, hardeners, preservatives, and the like has given a great deal of flexibility to ointment formulation. Although surface-active agents (i.e., surfactants) may be ionic or nonionic, the nonionic agents are widely used in dermatologic and pharmaceutical preparations. Polysorbate 80 (e.g., Tween 80) and Polyoxyl 40 Stearate represent such surfactants. Nonionic surfactants are generally less toxic and less irritating than ionic surfactants. Other advantages include their virtual neutrality, stability to freezing, stability to electrolytes, and ease of use. In general, the emulsion bases contain an aqueous phase, an emulsifying agent, and an oleaginous phase. The water phase of illustrative emulsion bases typically varies from 10 to 80% by weight of the total base. Glycerin, propylene glycol, or a polyethylene glycol is generally included with the aqueous phase to serve as a humectant, to reduce water loss through evaporation, and to lend a general softness to the creams. The addition of certain alcohols to emulsion base formulas also adds stability to the emulsion and imparts a smooth feel to the skin. Stearyl alcohol, a solid, increases the consistency of the ointment and permits the incorporation of more liquid components.

Due to their ability to become hydrated, such alcohols assist in water retention of emulsion bases. The oleaginous phase may contain one or more of the following or similar ingredients: petrolatum, fats, waxes, organic alcohols, polyglycol esters, or other grease-like substances. These substances are emulsified with the aqueous phase through the action of the surfactant. A few such emulsifiers include alkali soaps, alkyl sulfates, amine soaps, polyglycol esters, alkyl aryl sulfates, quaternary ammonium compounds, and the like. These emulsifying compounds aid in the dispersion of the fats and waxes in water and increase the stability of the ointments. Hydrophilic Ointment Base, Beeler's Base, and U.C.H. Base are illustrative O/W emulsion bases described herein. Commercially available O/W emulsion bases include Cetaphil® Cream (made by Galaderma Laboratories, L.P., Princeton, N.J.), Neobase (made by Neobase, Seattle, Wash.), Unibase® (made by Pfizer, New York, N.Y.), Dermovan, Phorsix Cream, Lubriderm® Cream (made by Pfizer, New York, N.Y.), and Velvachol® (available from Galderma Laboratories, Inc., Fort Worth, Tex.).

Water-soluble bases are anhydrous, soluble in water, water-removable, and greaseless, and will absorb water. These bases include those bases prepared from polyethylene glycols as well as semisolid preparations containing bentonite, colloidal magnesium aluminum silicate, and sodium alginate. Polyethylene glycol (PEG) compounds 1500, 1540, 4000, and 6000 are of interest in ointment and lotion formulations. PEG 1500 is a soft waxy solid, similar in consistency to petrolatum, with a congealing range of 40° C. to 45° C. PEG 1540 is a solid of consistency of beeswax and is intermediate in physical properties between the 1500 and 4000 PEGs. PEG 4000 has a congealing range of 53° C. to 56° C. and is most useful as a component of being an ointment base for, in addition to the general property of being an emulsifying and dispersing agent, it also adds to the consistency of the base. Both PEG 4000 and PEG 6000 are nonhygroscopic. PEG 6000 is a hard, translucent, waxy solid, and has a congealing range of 58° C. to 62° C.

Glyceryl monostearate is a polyhydric alcohol ester that has been widely used in cosmetic and ointment bases. It has a high melting point (56° C. to 58° C.) and is a good emulsifying agent. Glyceryl monostearate emulsions generally contain high water phases, usually above 60% by weight. It has the disadvantage of being incompatible with acids. Glyceryl Monostearate Base is described herein.

Cellulose derivatives, such as methylcellulose and hydroxyethyl cellulose, form colloidal solutions that resemble gums and mucilages, but are not as vulnerable to fungal or bacterial attack. Methylcellulose is dispersible in cold water, but in concentrated solutions will coagulate upon heating. Hydroxyethyl cellulose is more soluble at elevated temperatures so that viscosity of aqueous solutions decreases slightly on warming. Hydroxyethyl cellulose is a good protective colloid for aqueous dispersions of oils, waxes, and pigments. Sodium carboxymethylcellulose is another cellulose derivative frequently referred to as carboxymethyl cellulose or CMC. Sodium carboxymethylcellulose is an anionic compound and thereby may be used as a thickening or stabilizing agent for suspensions and for ointments of the emulsion type where the emulsifying agent is anionic or nonionic. Any of these cellulose derivatives may be used to stabilize ointment formulas, and they are commercially available in various viscosity types and with various degrees of substitution.

Sodium alginate is a hydrophilic colloid that is compatible with small amounts of alcohol, glycerin, polyglycols, wetting agents, and solutions of alkali carbonates. It functions satisfactorily under acid or alkaline conditions within the pH range of 4.5-10. It is possible to make sodium alginate solutions into semi-firm or firm gels by the addition of small amounts of soluble calcium salts, i.e., calcium gluconate, calcium tartrate, and calcium citrate. Ions of the alkaline earth metals will thicken or gelatinize sodium alginate solutions when present in low concentrations, while at high concentrations they will precipitate them. A 2.5% solution of sodium alginate is a satisfactory inert diluent for greaseless and other types of ointments.

Bentonite, a colloidal hydrated aluminum silicate, is insoluble in water, but when mixed with 8 to 10 parts of water it swells to produce a slightly alkaline gel resembling petrolatum. The consistency of the product may be regulated by varying the amounts of water added. Ointments prepared from bentonite and water alone are found to be slightly drying and unstable upon standing, but addition of a humectant, such as glycerin or sorbitol, in amounts up to about 10% by weight will retard this action. Ointments prepared from bentonite do not encourage mold growth, and they have the advantage of not spreading to the hair when applied to the scalp.

Colloidal magnesium aluminum silicate (e.g., Veegum®, R.T. Vanderbilt Company, Inc.) is an inorganic emulsifier, suspending agent, and thickener. Dispersions are slightly alkaline and are compatible with about 20 to 30% ethyl alcohol, isopropyl alcohol, acetone, and similar solvents. Glycols, such as glycerin and propylene glycol, are compatible at 40 to 50% concentrations.

Carbopol® 934 (carboxypolymethylene, made by B.F. Goodrich Chemical Co., Akron, Ohio) is an acid polymer that disperses readily in water to yield an acid solution of low viscosity. When the acid solution is neutralized with a suitable base, such as sodium bicarbonate, sodium hydroxide, or the like, a clear, stable gel results. Carbopol® 934 is inert physiologically and is neither a primary irritant nor a sensitizer. The thickening efficiency of Carbopol® 934 may be used in the preparation of such pharmaceuticals as creams, ointments, lotions, suspensions, and emulsions.

The skin care compositions of the present invention may also contain fragrances, proteins, colorants or coloring agents, vitamins, botanical extracts, glycolipids, polymers, copolymers, and the like, as are generally known in the art of making skin care products. The Cosmetic, Toiletry, and Fragrance Association's International Cosmetic Ingredient Dictionary and Handbook is an excellent source of information concerning such ingredients.

As used herein, "colorants" or "coloring agents" are agents that give skin care compositions a more pleasing appearance, and in addition help the manufacturer to control the product during its preparation and help the user to identify the product. Any of the approved certified water-soluble FD&C dyes, mixtures thereof, or their corresponding lakes may be used to color skin care compositions. A color lake is the combination by adsorption of a water-soluble dye to a hydrous oxide of a heavy metal, resulting in an insoluble form of the dye.

Partially Hydrolyzed Fucoidan

Brown seaweed, a source of fucoidan, grows in many oceans, including off the coasts of Japan and Okinawa, Russian coastal waters, Tonga, and other places. An excellent source of fucoidan is the limu moui sea plant growing in the waters of the Tongan islands. This brown seaweed contains many vitamins, minerals, and other beneficial substances and is particularly rich in fucoidan.

Typically, the brown seaweed grows in long angel hair stems with numerous leaves. The fucoidan ingredient is found in natural compositions on the cell walls of the seaweed, providing a slippery sticky texture that protects the cell walls from the sunlight.

In one embodiment, a kombu-type or mozuku-type seaweed is harvested from the coastal waters of the Tongan islands. These seaweeds can be manually harvested, including stems and leaves, by divers and cleaned to remove extraneous materials. The seaweed is then usually frozen in large containers and shipped to a processing plant.

In processing, the heavy outer fibers must first be broken down to provide access to the fucoidan component. If frozen, the seaweed material is first thawed. Then the seaweed material is placed in a mixing vat and shredded, while being hydrolyzed with acids and water. The material can optionally be sulfonated with sulfuric acid to help in breaking down the heavy cell fibers. The mixture is also buffered with citric acid and thoroughly blended to maintain suspension. The material may also be heated at atmospheric or greater than atmospheric pressure while mixing. The resulting puree is tested and maintained at a pH of about 2 to 4 so as to remain acidic, thus enhancing preservative and stability characteristics.

The puree may be used in preparing dietary supplement products. Alternately, the mixture may be frozen in small containers for later processing. The puree may be dried and added to the base before application to the tissue. The puree may be directly added to the base for application to the article. Further methods of adding constituents to the article are discussed below.

According to one embodiment, the present invention provides an article formulated with fucoidan compositions from seaweed, such as the limu moui seaweed plant, the Japanese mozuku seaweed, or Japanese kombu seaweed, or mixtures thereof. In another embodiment, the fucoidan may be partially hydrolyzed fucoidan. In yet another embodiment, the fucoidan may be sulfonated. In still another embodiment, the fucoidan compositions are present in selected embodiments in the amount of at least about 0.05 weight percent, or at least about 3 weight percent, or at least about 5 weight percent; and less than about 100 weight percent, or less than about 80 weight percent, or less than about 50 weight percent of the total weight of the moist application.

In a further embodiment, the partially hydrolyzed fucoidan may be derived from Tongan limu moui, Japanese hoku kombu (*Laminaria japonica*), wakame, or mozuku (*Cladosiphon* and *Nemacystus*). In still a further embodiment, the partially hydrolyzed fucoidan may be sulfonated.

Anti-Viral Agents

The tissue of the present invention may also include anti-viral agents. Certain viral infections are spread through bodily secretions. It is, therefore, an advantage to include anti-viral agents which neutralize viruses in a tissue that may be used to wipe or adsorb bodily secretions. U.S. Pat. No. 6,517,849, which is incorporated herein by a reference, discloses the addition of certain anti-viral agents to tissues.

The antiviral agent of the present invention may comprises pyrrolidone carboxylic acid. Pyrrolidone carboxylic acid, which is also referred to as pyroglutamic acid has two stereoisomers (D and L). Both stereoisomers are suitable for use in the present invention. Each or mixtures thereof are for use herein. Furthermore, blends of the two stereoisomers may also be used. The L stereoisomer is useful.

The D stereoisomer of pyroglutamic acid is also known by the following names: D-Proline, 5-oxo-(+)-2-Pyrrolidone-5-carboxylic acid, (+)-Pyroglutamic acid, (R)-2-Pyrrolidone-5-carboxylic acid, 5-Oxo-D-proline, D-2-Pyrrolidone-5-carboxylic acid, D-Pyroglutamic acid, D-Pyrrolidinonecarboxylic acid, and D-Pyrrolidonecarboxylic acid.

The L stereoisomer of pyroglutamic acid is also known by the following names: L-Proline, 5-oxo-(−)-2-Pyrrolidone-5-carboxylic acid, (−)-Pyroglutamic acid, (5S)-2-Oxopyrrolidine-5-carboxylic acid, (S)-(−)-2-Pyrrolidone-5-carboxylic acid, (S)-2-Pyrrolidone-5-carboxylic acid, (S)-5-Oxo-2-pyrrolidinecarboxylic acid, (S)-Pyroglutamic acid, 2-L-Pyrrolidone-5-carboxylic acid, 2-Pyrrolidinone-5-carboxylic acid, 5-Carboxy-2-pyrrolidinone, 5-Oxo-L-proline, 5-Oxoproline, 5-Pyrrolidinone-2-carboxylic acid, Glutimic acid, Glutiminic acid, L-2-Pyrrolidone-5-carboxylic acid, L-5-Carboxy-2-pyrrolidinone, L-5-Oxo-2-pyrrolidinecarboxylic acid, L-5-Oxoproline, L-Glutamic acid, .gamma.-lactam, L-Glutimic acid, L-Glutiminic acid, L-Pyroglutamic acid, L-Pyrrolidinonecarboxylic acid, L-Pyrrolidonecarboxylic acid, Oxoproline, PCA, Pidolic acid, Pyroglutamic acid, Pyrrolidinonecarboxylic acid, Pyrrolidone-5-carboxylic acid, and Pyrrolidonecarboxylic acid.

The DL form of pyroglutamic acid (a mixture of the D and L stereoisomers) is known by the following names: DL-Proline, 5-oxo-(.+−.)-2-Pyrrolidone-5-carboxylic acid, (.+−.)-Pyroglutamic acid, 5-Oxo-DL-proline, DL-2-Pyrrolidinone-5-carboxylic acid, DL-2-Pyrrolidone-5-carboxylic acid, DL-Pyroglutamate, DL-Pyroglutamic acid, DL-Pyrrolidonecarboxylic acid, and Oxoproline. The DL form is also commercially available under the tradename Ajidew™ A 100.

In addition to pyrrolidone carboxylic acid, other organic acids may be optionally added to the antiviral composition. These include but are not limited to organic acids such as ascorbic acid and other carboxylic acids.

Suitable other carboxylic acids include but are not limited to alpha hydroxy acids such as $C_1$ to $C_{12}$ saturated, unsaturated, or mixtures thereof of carboxylic acids possessing 1 to 4 carboxylic acid groups and having at least one hydroxyl group substituted on the $C_2$ alpha carbon with additional hydroxyl and other functionalities (i.e.; phenyl, amino, alkyl, etc.) optionally bound along the carbon chain and aromatic ring(s). A non-inclusive list of alpha hydroxy acids which may be used includes: 2-hydroxyhexanoic acid, 2-hydroxyoctanoic acid, 2-hydroxydecanoic acid, 2-hydroxydodecanoic acid, 2-hydroxycaprylic acid, citric acid, tartaric acid, mandelic acid, malic acid, glycolic acid, lactic acid, gluconic acid, hydroxycaprylic acid, 2-hydroxypropionic acid, 2-hydroxybutanoic acid, 2-hydroxypentanoic acid, and mixtures thereof.

Other examples of carboxylic acids useful with this invention include beta hydroxy acids such as $C_1$ to $C_{12}$ saturated, unsaturated, aromatic, or mixtures thereof of carboxylic acids possessing 1 to 4 carboxylic acid groups and having at least one hydroxyl group substituted on the $C_3$ beta carbon with additional hydroxyl and other functionalities (i.e.; phenyl, amino, hydroxyl, alkyl, etc.) optionally bound along the carbon chain or aromatic ring(s). A non-inclusive list of beta hydroxy acids useful with this invention includes: 3-hydroxyhexanoic acid, 3-hydroxyoctanoic acid, 3-hydroxydecanoic acid, 3-hydroxydodecanoic acid, 3-hydroxycaprylic acid, salicylic acid, 5-octanoyl salicylic acid, 3-hydroxybutanoic acid, 3-hydroxypentanoic acid, 3-hydroxypropionic acid, and mixtures thereof.

A non-inclusive list of other carboxylic acids useful with this invention includes $C_1$ to $C_{12}$ saturated, unsaturated, aromatic, or mixtures thereof of carboxylic acids possessing 1 to 4 carboxylic acid groups with optional functional groups (i.e.; phenyl, amino, hydroxyl, alkyl, etc.) substituted along the carbon chain or on the aromatic ring(s) such as propionic acid, hexanoic acid, octanoic acid, decanoic acid; $C_1$ to $C_{12}$ carboxylic acids possessing 1 to 4 carboxylic acid groups wherein a hydroxyl group(s) is substituted on carbon number(s) $C_4$ or above such as 4-hydroxyhexanoic acid, 5,6-dihydroxyhexanoic acid, 6-hydroxyhexanoic acid, 4-hydroxyoctanoic acid, 5-hydroxyoctanoic acid, 6-hydroxyoctanoic acid, 6,7,8-trihydroxyoctanoic acid, 8-hydroxyoctanoic acid, 4-hydroxydecanoic acid, 5-hydroxydecanoic acid, 6-hydroxydecanoic acid, 7-hydroxydecanoic acid, 8-hydroxydecanoic acid, 9-hydroxydecanoic acid, 10-hydroxydecanoic acid, 4-hydroxydodecanoic acid, 5-hydroxydodecanoic acid, 6-hydroxydodecanoic acid, 1-hydroxydodecanoic acid, and 12-hydroxydodecanoic acid; benzoic acid; phthalic acid; acetylsalicylic acid; dehydroacetic acid; sorbic acid; succinic acid; glutaric acid; adipic acid; sebacic acid; maleic acid; folic acid; acetic acid; ethylenediaminetetraacetic acid; glycolic acid; and mixtures thereof.

Metal salts may also be used as an optional component of the antiviral agent of the present invention. Suitable metal salts include, but are not limited to, salts of metals selected from the groups consisting of Groups I(A, B), II(A, B), IIIA, IV(A, B), VIB, VIII, rare earth compounds, and combinations thereof. Metal salts may include salts of metals selected from the group consisting of Mn, Ag, Zn, Sn, Fe, Cu, Al, Ni, Co, Ti, Zr, Cr, La, Bi, K, Cd, Yb, Dy, Nd, Ce, Ti, Pr, and combinations thereof. Even more useful, metal salts include salts of metals selected from the group consisting of Mn, Ag, Zn, Sn, Fe, Cu, Al, Ni, Co, Ti, Zr, Cr, La, and combinations thereof. The metal salts may include salts of metals selected from the group consisting of Cu, Fe, and combinations thereof.

More particularly, the metal salts include, but are not limited to, dermatologically acceptable metal chelates and salts like bishistidine complexes, bromides, chondroitin sulfate, chromites, cyanides, dipiocolinates, ethylhexanoates, glycerolate complex, methoxides, polyphosphonates, paraphenolsulfonates, perchlorates, phenolsulfonates, selenides, stearates, thiocyanates, tripolyphosphates, tungstates, phosphates, carbonates, para-aminobenzoate, paradimethylaminobenzoates, hydroxides, para-methoxycinnamate, naphthenates, stearates, caprates, laurates, myristates, palmitates, oleates, picolinates, pyrithiones, fluorides, aspartates, gluconates, iodides, oxides, nitrites, nitrates, phosphates, pyrophosphates, sulfides, mercaptopyridine-oxides (e.g., zinc pyrithione), nicotinates, and nicotinamides, hinokitiol, acetates, ascorbates, chlorides, benzoates, citrates, fumarates, gluconates, glutarates, lactates, malates, malonates, salicylates, succinates, sulfates, undecylates, and combinations thereof.

Other Optional Ingredients

The tissue may include any number of optional ingredients that are known in the art of skin moisturizing. For example, a well-known herb used for skin healing is aloe. Aloe includes the juice of the leaves of any of the more than 240 species of aloe, or combinations thereof. Aloe with particular nutritional value comes from the Aloe Barbadensis. The Aloe Barbadensis with the most recognized nutritional value is the Aloe barbadensis Miller. Aloe has been used in topical and internal uses. In one embodiment, the aloe present in the composition includes powdered aloe. Commercial sources of the dry powdered aloe of the present invention are available, for example, from Aloe Laboratories, Harlingen, Tex., USA and NHK Laboratories, Santa Fe Springs, Calif.

Other optional ingredients may include all-natural ingredients. Some examples of other ingredients include: honey, mangosteen, witch hazel, sage, piper, clove, ginger, red pepper, willow, rhubarb, sesame, chamomile, propolis, thyme, lavender, cinnamon oil, flower or blossom oils, olive oil, palm oil, coconut oil, beeswax, and so forth. One particularly beneficial natural ingredient is a derivative of the mangosteen plant. According to one embodiment, the present invention includes from about 0.01 to about 10 weight percent of a derivative of the mangosteen plant.

The Mangosteen plant (*Garcinia mangostana* L.) is a tropical fruit-bearing plant named after the French explorer Laurent Garcin. Many of the benefits of the mangosteen plant and its derivatives are described in U.S. Pat. No. 6,730,333, which is herein incorporated by a reference. Over the years, the mangosteen plant has been used in a number of different ways. The timber is used for cabinets, building materials, fencing and furniture. The pericarp, containing pectin, tannins, resins and a yellow latex, is used in tanning and dyeing leather black. The fruit pulp is mostly used as a dessert, but can also be canned or made into preserves. However, when removing the fruit pulp from the rind, care must be taken to prevent the tannins and resins of the cut pericarp from contacting the fruit pulp. The mangosteen rind, leaves and bark have also been used as ingredients in folk medicine in areas where the plant grows indigenously. The thick mangosteen rind is used for treating catarrh, cystitis, diarrhea, dysentery, eczema, fever, intestinal ailments, itch, and skin ailments. The mangosteen leaves arc used by some natives in teas and other decoctions for diarrhea, dysentery, fever, and thrush. It is also known that concoctions of mangosteen bark can be used for genitourinary afflictions and stomatosis.

Some of the medicinal properties of the *Garcinia mangostana* L. plant have been the subject of pharmacological and clinical studies. These studies have isolated chemical constituents in the mangosteen leaves, wood, pericarp and seed aril, which were found to contain the following biologically active compounds, among others: 1,6-dihydroxy-3-methoxy-2-(3-methyl-2-butenyl) xanthone, 1,5,8-trihydroxy-3-methoxy-2-(3-methyl-2-butenyl) xanthone, maclurin, 1,3,6,7-tetrahydroxy xanthone, 1,3,6,7-tetrahydroxy xanthone-O-β-D-glucoside, chrysanthemin, cyaniding-3-O-β-D-sophoroside, 8-deoxygartanin, 1,5-dihydroxy-2-isopentenyl-3-methoxy xanthone, 1,7-dihydroxy-2-isopentenyl-3-methoxy xanthone, 5,9-dihydroxy-8-methoxy-2,2-dimethyl-7-(3-methylbut-2-enyl)2(H),6(H)-pyrano (3,2,6)-xanthen-6-one, fructose, garcinone A, B, C, D and E, gartanin, glucose, cis-hex-3-enyl acetate, 3-isomangostin, 3-isomangostin hydrate, 1-isomangostin, 1-isomangostin hydrate, kolanone, mangostin, β-mangostin, α-mangostin, mangostin-3,6-di-O-gulcoside, normangostin, sucrose, tannins, BR-xanthone-A, BR-xanthone-B, calabaxanthone demethylcalabaxanthone, 2-(γ,γ-dimethylallyl)-1,7-dihydroxy-3-methoxyxanthone, 2,8-bis-(γ,γ-dimethylallyl)-1,3,7-trihydroxyxanthone, 1,3,5,8-tetrahydroxy-2,4-diprenylxanthone, and mangostanol. Many of these chemical constituents are xanthones, which are biologically active compounds that are receiving increasing interest in pharmacological studies for a variety of health benefits.

Method of Treating the Tissue

In preparing virucidal tissue products according to the present invention, the base and the partially hydrolyzed fucoidan, along with the optional ingredients such as the antiviral composition may be applied to at least one surface of a tissue paper web. They may be applied uniformly or discretely to the tissue paper web. A non-limiting example of discrete addition to the tissue paper web is disclosed in U.S. Pat. No. 5,814,188 issued to Vinson et al. on Sep. 29, 1998, the disclosure of which is incorporated herein by reference.

The base, partially hydrolyzed fucoidan, and other optional ingredients may be applied in a continuous pattern or discontinuous pattern. Suitable application methods include those disclosed in U.S. Pat. No. 4,481,243 issued to Allen on Nov. 6, 1984; U.S. Pat. No. 5,720,966 issued to Ostendorf on Feb. 24, 1998; and U.S. Pat. No. 5,814,188 issued to Vinson et al. on Sep. 29, 1998, the disclosures of which are incorporated herein by reference.

Suitable methods include spraying, dipping, soaking, printing (e.g., flexographic printing), coating (e.g., gravure coating), extrusion, or combinations of these application techniques, e.g. spraying the composition on a rotating surface, such as a calendar roll, that then transfers the composition to the surface of the paper web. The composition can be applied either to one surface of the tissue paper web, or both surfaces.

The compositions of this invention can also be applied non-uniformly to the surface(s) of the tissue paper web. By "non-uniform" is meant that the amount, pattern of distribution, etc. of the antiviral agent can vary over the surface of the paper. For example, some portions of the surface of the tissue paper web can have greater or lesser amounts of the composition, including portions of the surface that do not have any composition on it.

An example of non-uniform application is where the tissue structure contains differing amounts and differing compositions of various formulations throughout its structure or alternatively where some zones may contain no lotion at all as taught by U.S. Pat. No. 4,481,243 issued to Allen on Nov. 6, 1984 which is incorporated herein by reference.

Partially hydrolyzed fucoidan, and other optional ingredients are applied to the tissue. The tissue may include from about 0.05 to about 50 weight percent partially hydrolyzed fucoidan.

It is understood that the above-described embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

Thus, while the present invention has been fully described above with particularity and detail in connection with what is presently deemed to be the most practical embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims.

EXAMPLES

The following are examples of the preparation of seaweed to provide a fucoidan puree for use in skin care products, and skin care formulations prepared from the fucoidan puree. These examples are merely illustrative and are not meant to be limiting in any way.

The present invention may be embodied in other specific forms without departing from its spirit or essential characteristics. The described embodiments are to be considered in all respects only as illustrative and not restrictive. The scope of the invention is, therefore, indicated by the appended claims, rather than by the description or examples. All changes that come within the meaning and range of equivalency of the claims are to be embraced within their scope.

In order to demonstrate the practice of the present invention, the following examples have been prepared. Some of the examples may be labeled as "prophetic." It is assumed that such examples may not have been actually yet performed. The examples should not, however, be viewed as limiting the scope of the invention. The claims will serve to define the invention.

Prophetic Example 1

Preparation of Fucoidan Puree Composition

Tongan limu moui seaweed is manually harvested, cleaned to remove extraneous material, frozen, and shipped to a processing plant. At the plant, the frozen seaweed is thawed, weighed, and placed in a stainless steel mixer with aqueous buffer and optionally sulfuric acid according to any of the sets of conditions set out in Table 1. The ingredients are then mixed at 50-75 rpm with a medium shear mixer (propeller type). While mixing, the mixture is heated to 37° C. to 95° C. for a selected period of time (usually 5 min to 8 hr). At that point, heating is discontinued, but mixing is continued for 0.5-10 hours to dissipate heat and micronize the seaweed strands. The cooled mixture is then filtered to remove insoluble material, and the filtrate was covered and mixed at room temperature for about 4-72 hours. The pH of the resulting puree is determined to be about pH 2.0 to 4.0, and refractometry typically shows a Brix value of 2-4. The puree comprising partially hydrolyzed fucoidan is then frozen and stored. If sulfuric acid is added during hydrolysis, the partially hydrolyzed fucoidan is sulfonated.

TABLE 1

|  | Trial I | Trial II | Trial III | Trial IV | Trial V | Trial VI | Trial VII |
|---|---|---|---|---|---|---|---|
| pH | 2.0-2.4 | 2.2-2.5 | 2.4-2-7 | 2.6-3.0 | 2.9-3.2 | 3.2-3.6 | 3.6-4.0 |
| sulfuric acid | — | 0.01N | — | 0.001N | 0.004N | — | 0.001 |
| seaweed | 20 wt % | 10 wt % | 25 wt % | 40 wt % | 33 wt % | 15 wt % | 42 wt % |
| temp | 37 C. | 42 C. | 50 C. | 60 C. | 75 C. | 80 C. | 95 C. |
| heating time | 5 hr | 4 hr | 4 hr | 3 hr | 35 min | 20 min | 15 min |
| filtrate mixing | 24 hr, 37 C. | 16 hr, 37 C. | 72 hr, 22 C. | 24 hr, 22 C. | 48 hr, 22 C. | 36 hr, 22 C. | 8 hr, 22 C. |

Prophetic Example 2

Silicone Gibson Base

The following formula illustrates a silicone base that may be used in a cream or lotion according to the present invention. Silicone Gibson base comprises 15 parts by weight of cetyl alcohol, 1 parts by weight of sodium lauryl sulfate, 40 parts by weight of dimethylpolysiloxane polymer (1000 cps), 43 parts by weight purified water, 0.25 parts by weight methylparaben, and 0.15 parts by weight propylparaben. The aqueous mixture of the sodium lauryl sulfate and the parabens is warmed to 75° C., and then it is slowly added to warmed (25° C.) cetyl alcohol-silicone mixture. The resulting mixture is stirred until it congeals.

Prophetic Example 3

Vanisil Silicone Ointment Base

The following formula illustrates a silicone base that may be used in a cream or lotion according to the present invention. Vanisil silicone ointment base comprises 10 parts by weight stearic acid, 2 parts by weight synthetic Japan wax, 20 parts by weight dimethylpolysiloxane polymer (1000 cps), 0.5 parts by weight potassium hydroxide, 0.025 parts by weight methylparaben, 0.015 parts by weight propylparaben, and 67.5 parts by weight distilled water.

Prophetic Example 4

Zopt Emollient Cream

The following formula illustrates a W/O emulsion absorption base that may be used according to the present invention. Zopf emollient cream comprises 41 parts by weight of white petrolatum, 3 parts by weight of microcrystalline wax, 10 parts by weight of fluid lanolin, 4.75 parts by weight sorbitan monooleate, 0.25 parts by weight of polysorbate 80, and 41 parts by weight purified water. The aqueous dispersion of sorbitan monooleate and polysorbate 80 is warmed to 75° C. and then slowly added to the melted wax, white petrolatum, and fluid lanolin. The resulting mixture is stirred until it congeals.

Prophetic Example 5

Hoch Formula

The following formula illustrates an O/W emulsion absorption base that may be used according to the present invention. Hoch formula comprises phase A comprising 5 parts by weight of fluid lanolin, 35 parts by weight of castor oil, 2 parts by weight of sorbitan monostearate, 36.7 parts by weight of mineral oil, 4 parts by weight of stearic acid, and 0.2 parts by weight of propylparaben; and phase B comprising 1 parts by weight of polyethylene 20 sorbitan monostearate, 0.9 parts by weight of triethanolamine, 0.2 parts by weight of methylparaben, and 15 parts by weight of purified water. Phase A is heated to 78° C., and phase B is heated to 70° C. Then, phase B is added to phase A and the resulting mixture is stirred until it cools to 25° C.

Prophetic Example 6

Hydrophilic Petrolatum Base

The following formula illustrates an absorption base that may be used according to the present invention. Hydrophilic petrolatum base comprises 30 parts by weight of cholesterol, 30 parts by weight of stearyl alcohol, 80 parts by weight of white wax, and 860 parts by weight of white petrolatum. The stearyl alcohol, white wax, and white petrolatum are melted together on a steam bath, and then the cholesterol is added and stirred into the mixture until the cholesterol completely dissolves. The mixture is then removed from the bath and stirred until it congeals.

Prophetic Example 7

Wool Alcohols Base

The following formula illustrates an absorption base that may be used according to the present invention. Wool alcohols ointment base comprises 60 parts by weight wool alcohols, 240 parts by weight hard paraffin, 100 parts by weight white or yellow soft paraffin, and 600 parts by weight liquid paraffin. The ingredients are mixed together and stirred until cold.

Prophetic Example 8

Aquabase Ointment

The following formula illustrates an absorption base that may be used according to the present invention. Aquabase ointment comprises 30 parts by weight of cholesterol, 30 parts by weight of cottonseed oil, and 940 parts by weight of white petrolatum. The white petrolatum and cottonseed oil are heated to 145° C. and then removed from the heat. The cholesterol is then added and stirred until it is almost congealed. Then the ointment is placed in suitable containers.

Prophetic Example 9

Emulsion Base

The following formula illustrates an emulsion base that may be used according to the present invention. Many dermatologic and cosmetic preparations contain amine soaps as emulsifying agents. These anionic emulsifiers are advantageous as compared to sodium and potassium soaps because they yield emulsions having a relatively low pH of about 8.0. Triethanolamine is generally used, along with a fatty acid, to produce the fatty acid amine soap. Triethanolamine usually contains small amounts of ethanolamine and diethanolamine. It combines stoichiometrically with fatty acids. Semisolid O/W bases containing triethanolamine soaps are generally prepared by dissolving the triethanolamine in water and then adding this solution to the oil phase with stirring. A typical formula for such a base comprises 18 parts by weight stearic acid, 4 parts by weight of cetyl alcohol, 2 parts by weight of triethanolamine, 5 parts by weight of glycerin, and 71 parts by weight of distilled water.

Prophetic Example 10

Coal Tar Ointment Base

The following formula illustrates an emulsion base that may be used according to the present invention. Coal tar ointment base contains a surfactant, i.e., polysorbate 80, which serves the dual purpose of a dispersing agent and aiding in removal of the ointment from the skin. Coal tar ointment comprises 10 parts by weight coal tar, 5 parts by weight polysorbate 80, and 985 parts by weight zinc oxide paste. The coal tar is blended with the polysorbate 80, and this blend is then mixed with the zinc oxide paste.

Prophetic Example 11

Hydrophilic Ointment Base

The following formula illustrates an emulsion base that may be used according to the present invention. Hydrophilic ointment base comprises 0.25 parts by weight methylparaben, 0.15 parts by weight propylparaben, 10 parts by weight sodium lauryl sulfate, 120 parts by weight propylene glycol, 250 parts by weight stearyl alcohol, 250 parts by weight white petrolatum, and 370 parts by weight water. The stearyl alcohol and white petrolatum are melted on a steam bath and warmed to about 75° C. The other ingredients, previously dissolved in the water, are warmed to 75° C. and then added with stirring until the mixture congeals.

Prophetic Example 12

Beeler's Base

The following formula illustrates an O/W emulsion base that may be used according to the present invention. Beeler's base comprises 15 parts by weight cetyl alcohol, 1 parts by weight white wax, 10 parts by weight propylene glycol, 2 parts by weight sodium lauryl sulfate, and 72 parts by weight water. The cetyl alcohol and white wax are melted in the propylene glycol on a water bath, and the resulting mixture is heated to about 65° C. The sodium lauryl sulfate is dissolved in the water and also heated on water bath to about 65° C. The oil phase is slowly added to the well-stirred water phase, and stirring is continued on the water bath for about 10 min. The emulsion is then removed from the water bath and stirring is continued to the point of congealing.

Prophetic Example 13

U.C.H. Base

The following formula illustrates an emulsion base that may be used according to the present invention. U.C.H. base comprises 6.4 parts by weight cetyl alcohol, 5.4 parts by weight stearyl alcohol, 1.5 parts by weight sodium lauryl sulfate, 14.3 parts by weight white petrolatum, 21.4 parts by weight mineral oil, and 50 parts by weight water. The alcohols are melted together over a water bath at 65° C., then the sodium lauryl sulfate is add with stirring. Next the white petrolatum and the mineral oil are added with continued heating of the mixture until it is completely melted. This mixture is then cooled to room temperature and the water is added with constant mixing to result in the emulsion.

Prophetic Example 14

Base A

The following formula illustrates an anhydrous emulsifiable solid mixture. Anhydrous solid mixture A is made by melting together 53 parts by weight of stearyl alcohol, 7 parts by weight of cetyl alcohol, 38.6 parts by weight of PEG 400, and 1.4 parts by weight of sodium lauryl sulfate. These ingredients are melted and stirred vigorously until completely solidified. Stirring is continued to insure complete mixing of the ingredients and for the production of a granular product. Base A is made by melting 50 parts by weight of the granular solid mixture A, heating it to 70-75° C., and then adding it to 50 parts by weight of an aqueous mixture at the same temperature. The mixture is stirred until the emulsion begins to solidify and cools to 40° C. The resulting base is a white, semisolid 0/W emulsion of ointment-like consistency. It is non-greasy and washable with water. The emulsion is stable up to 55-60° C., exhibits a good sheen, and exhibits good lubricity when applied to skin.

Prophetic Example 15

Base B

The following formula illustrates an anhydrous emulsifiable solid mixture. Anhydrous solid mixture B is made by melting together 64.7 parts by weight of stearyl alcohol, 8.6 parts by weight of cetyl alcohol, 13 parts by weight of PEG 1000 monostearate, 8.7 parts by weight of PEG 1540, and 5 parts by weight of anhydrous lanolin. These ingredients are melted and stirred vigorously until completely solidified. Stirring is continued to insure complete mixing of the ingredients and for the production of a granular product. Base B is made by melting 40 parts by weight of the granular solid mixture B, heating it to 70-75° C., and then adding it to 60 parts by weight of an aqueous mixture at the same temperature. The mixture is stirred until the emulsion begins to solidify and cools to 40° C. The resulting base is a white, semisolid O/W emulsion of ointment-like consistency. It is non-greasy and washable with water. The emulsion is stable up to 55-60° C. and exhibits good lubricity when applied to skin.

Prophetic Example 16

Aqueous Cream Base

The following formula illustrates an emulsion base that may be used according to the present invention. Aqueous cream base is an emulsion base prepared from 30% by weight of emulsifying ointment and 70% by weight of water. Emulsifying ointment comprises 30 parts by weight emulsifying wax, 20 parts by weight liquid paraffin, and 50 parts by weight white soft paraffin. Emulsifying wax comprises 90 parts by weight cetostearyl alcohol, 10 parts by weight sodium lauryl sulfate, and 4 parts by weight purified water.

Prophetic Example 17

Polyethylene Glycol Ointment Base

The following formula illustrates a water-soluble base that may be used according to the present invention. Polyethylene glycol ointment base comprises 400 parts by weight of PEG 4000 and 600 parts by weight of PEG 400. The two ingredients are heated on a water bath to 65° C., and then the mixture is allowed to cool with stirring until it congeals. If a firmer preparation is desired, up to 100 parts by weight of the PEG 400 may be replaced with an equal amount of PEG 4000. If 6-25% by weight of an aqueous solution is to incorporated in this polyethylene ointment, 50 parts by weight of the PEG 4000 is replaced with an equal amount of stearyl alcohol.

Prophetic Example 18

Base G

The following formula illustrates a water-soluble base that may be used according to the present invention. The addition of an ester of polyethylene glycol to a polyethylene glycol ointment yields a water-removable, emulsifiable ointment base. An illustrative emulsifiable glycol ointment base (Base G) of this type comprises 26 parts by weight polyethylene glycol 400 monostearate, 37 parts by weight PEG 400, and 37 parts by weight PEG 4000. The glycols are mixed and melted at about 65° C. This mixture is then stirred while cooling to about 40° C. The polyethylene glycol 400 monostearate is melted at about 40° C. and then added to the liquid glycol mixture with stirring until a uniform ointment is obtained. Water (10-15% by weight) may be incorporated into Base G.

Prophetic Example 19

Base III

The following formula illustrates a water-soluble base that may be used according to the present invention. Surfactants and water may be added to a polyethylene glycol ointment without impairing the water removability of the base. Base III represents a typical formula of this type: 50 parts by weight PEG 4000, 40 parts by weight PEG 400, 1 parts by weight sorbitan monopalmitate, and 9 parts by weight water. The sorbitan monopalmitate and the polyethylene glycols are warmed together on a water bath to 70° C. and the water heated to the same temperature is then added. The emulsion is stirred until it congeals.

Prophetic Example 20

Modified Landon-Zopf Base

The following formula illustrates a water-soluble base that may be used according to the present invention. Modified Landon-Zopf base comprises 20 parts by weight PEG 4000, 34 parts by weight stearyl alcohol, 30 parts by weight glycerin, 15 parts by weight water, and 1 parts by weight sodium lauryl sulfate. The PEG 4000, stearyl alcohol, and glycerin are heated on a water bath to 75° C. This mixture is then added in small quantities with stirring to the water, which contains the sodium lauryl sulfate and has also been heated to 75° C. Moderate stirring is continued until the base has congealed.

Prophetic Example 21

Canadian Base

The following formula illustrates a water-soluble base that may be used according to the present invention. Canadian base comprises 11.2 parts by weight PEG 4000, 20.8 parts by weight stearyl alcohol, 17 parts by weight glycerin, 0.6 parts by weight sodium lauryl sulfate, and 50.4 parts by weight water. The PEG 4000, stearyl alcohol, and glycerin are heated on a water bath to 70° C. The water, which contains the sodium lauryl sulfate and has been previously heated to 70° C., is added and the mixture is stirred until the base congeals.

Prophetic Example 22

Base IV

The following formula illustrates a water-soluble base that may be used according to the present invention. Base IV comprises 42.5 parts by weight PEG 4000, 37.5 parts by weight PEG 400, and 20 parts by weight 1,2,6-hexanetriol. The PEG 4000 is heated with the 1,2,6-hexanetriol is heated on a water bath to 60-70° C. This mixture is added to the PEG 400 at room temperature with vigorous stirring. The, occasional stirring is continued until solidification takes place.

Prophetic Example 23

Glyceryl Monostearate Base

The following formula illustrates a water-soluble base that may be used according to the present invention. Glyceryl monostearate base comprises 10 parts by weight mineral oil, 30 parts by weight white petrolatum, 10 parts by weight glyceryl monostearate S.E., 5 parts by weight cetyl alcohol, 5 parts by weight glycerin, and 40 parts by weight water.

Prophetic Example 24

Lubricating Jelly Base

The following formula illustrates a water-soluble base that may be used according to the present invention. Lubricating jelly base comprises 1 g methocel 90 HC 4000, 0.3 g Carbopol® 934, sodium hydroxide as pH 7.0, 20 ml propylene glycol, 0.15 g methylparaben, and purified water as 100 parts by weight. The methocel is added slowly to 40 ml of hot water (80-90° C.) and agitated for 5 min. After cooling, the solution is refrigerated overnight. The Carbopol® 934 is dissolved in 20 ml of water, and 1% sodium hydroxide is added slowly with cautious stirring to avoid incorporation of air, until a pH of 7.0 is obtained, and then water is added to a total volume of 40 ml. The methylparaben is dissolved in the propylene glycol. Finally the methocel, Carbopol®, and methylparaben solutions are mixed cautiously to avoid incorporation of air.

Prophetic Example 25

Universal O/W Ointment Base

The following formula illustrates a water-soluble base that may be used according to the present invention. Universal O/W ointment base comprises 0.05 parts by weight calcium citrate, 3 parts by weight sodium alginate, 0.20 parts by weight methylparaben, 45 parts by weight glycerin, and sufficient distilled water to make a total of 100 parts by weight. The calcium citrate and the methylparaben are dissolved in the water. The glycerin is mixed with the sodium alginate to form a smooth paste. The aqueous mixture is added to the paste and is stirred until a smooth, stiff preparation is obtained. The base is then set aside for several hours until thickening is complete.

Prophetic Example 26

Hollander and McClanahan Base

The following formula illustrates a water-soluble base that may be used according to the present invention. Hollander and McClanahan base comprises 32 parts by weight petrolatum, 13 parts by weight bentonite, 0.5 parts by weight sodium lauryl sulfate, 54 parts by weight water, and 0.1 parts by weight methylparaben.

Prophetic Example 27

MGH Ointment Base

The following formula illustrates a water-soluble base that may be used according to the present invention. MGH ointment base comprises 15 parts by weight polyethylene glycol 200 monostearate, 2.5 parts by weight colloidal magnesium stearate silicate (Veegum), 1 part by weight polysorbate 80, 0.1 parts by weight methylparaben, and 81.4 parts by weight purified water.

Prophetic Example 28

Lotion Base

The following formula illustrates a water-soluble base that may be used according to the present invention. Lotion base comprises 1 part by weight Veegum, 0.85 parts by weight sodium carboxymethylcellulose, 90.15 parts by weight water, 3 parts by weight glycerin, and 5 parts by weight dioctyl sodium sulfosuccinate (1% solution). All the dry ingredients are mixed with water and glycerin in a blender for 1 min. The mixture is then removed from the blender and the dioctyl sodium sulfosuccinate is added.

Prophetic Example 29

Cold Cream Base

The following formula illustrates a cold cream according to an embodiment of the present invention. A cold cream base comprises 6 parts by weight spermaceti, 6 parts by weight beeswax, 10 parts by weight Carbopol® 934, 4.75 parts by weight sodium carbonate, 5 parts by weight rose water, 0.02 parts by weight rose oil, 56 parts by weight expressed almond oil, and 20 parts by weight distilled water.

Prophetic Example 30

Hand Lotion Base

The following formula illustrates a hand lotion according to an embodiment of the present invention. A hand lotion base comprises 24.75 ml propylene glycol, 1 ml triethanolamine, 12 ml water, 1.5 g oleic acid, 10.5 g polyethylene glycol 400 monostearate, 10 ml silicone fluid D.C. 200, and 50 g Carbopol® 9342% mucilage.

Prophetic Example 31

White Lotion Base

The following formula illustrates a hand lotion according to an embodiment of the present invention. White lotion base comprises 40 parts by weight zinc sulfate, 40 parts by weight sulfurated potash, and sufficient purified water to make 1000 parts by weight. The zinc sulfate and the sulfurated potash are dissolved separately, each in 450 parts by weight of purified water, and then each solution is filtered. The sulfurated potash solution is then added slowly to the zinc sulfate solution with constant stirring. Then the remainder of the water is added, and the lotion is mixed.

What is claimed is:

1. A composition consisting of tissue paper, partially hydrolyzed fucoidan, mangosteen extract and olive oil.

2. A composition consisting of tissue paper, partially hydrolyzed fucoidan, mangosteen extract and cottonseed oil.

3. A composition consisting of tissue paper, partially hydrolyzed fucoidan, mangosteen extract and persic oil.

4. A composition consisting of tissue paper, partially hydrolyzed fucoidan, mangosteen extract and sesame oil.

* * * * *